United States Patent [19]

Clarke et al.

[11] Patent Number: 4,539,202
[45] Date of Patent: Sep. 3, 1985

[54] DERIVATIVES OF CLAVULANIC ACID, A PROCESS FOR THEIR PREPARATION AND THEIR USE

[75] Inventors: Brian P. Clarke, Kingswood; John B. Harbridge, Coulsdon; Irene Stirling, Reigate, all of England

[73] Assignee: Beecham Group p.l.c., England

[21] Appl. No.: 478,326

[22] Filed: Mar. 24, 1983

Related U.S. Application Data

[62] Division of Ser. No. 176,161, Aug. 7, 1980, abandoned.

[51] Int. Cl.³ .............................................. A61K 35/00
[52] U.S. Cl. .................................................. 424/114
[58] Field of Search ........................................ 424/114

[56] References Cited

PUBLICATIONS

Chemical Abstracts 90:168574x, (1978).

Primary Examiner—Jerome D. Goldberg
Attorney, Agent, or Firm—Jacobs & Jacobs

[57] ABSTRACT

The compounds of the formula (II):

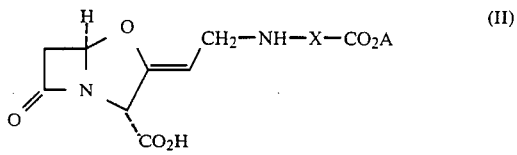

or pharmaceutically acceptable salts or esters thereof wherein A is a hydrogen atom or an esterifying radical; X is an alkyl group of 1–12 carbon atoms optionally substituted by a hydroxy, amino, acylamino of $C_{1-6}$ alkoxy group, which substituents are not on the carbon atom adjacent to the nitrogen atom; or a $C_{5-7}$ cycloalkyl group; or a phenylalkyl group wherein the carbon atom content of the alkyl part is 1–6 and the phenyl part is optionally substituted with a fluorine, bromine, chlorine, $C_{1-6}$ alkyl, or $C_{1-6}$ alkoxy; with the proviso that when X represents an optionally substituted phenylalkyl group and A represents $C_{1-3}$ alkyl, then the —$CO_2A$ group is attached to the alkyl part of the phenylalkyl group; have been found to be β-lactamase inhibitors and antibacterial agents. Their preparation and use is described.

12 Claims, No Drawings

DERIVATIVES OF CLAVULANIC ACID, A PROCESS FOR THEIR PREPARATION AND THEIR USE

This application is a division of application Ser. No. 176,161 filed Aug. 7, 1980 and now abandoned.

This invention relates to a novel class of clavulanic acid derivatives and in particular to a class of carboxyl-substituted alkylamine derivatives and carboxyl-substituted aralkylamine derivatives of clavulanic acid. These compounds have antibacterial and β-lactamase inhibitory properties and are therefore of use in the treatment of bacterial infections either alone or in combination with other antibacterial agents such as penicillins or cephalosporins.

Some carboxyl-substituted aralkylamine derivatives are known from W German OLS No. 2817085 (equivalent to French Pat. No. 2387986, Japanese Patent Application No. 48292/78 and U.S. patent application Ser. No. 896441) and European Application No. 79301618.9. W German OLS No. 2817085 discloses inter alia compounds of formula (I):

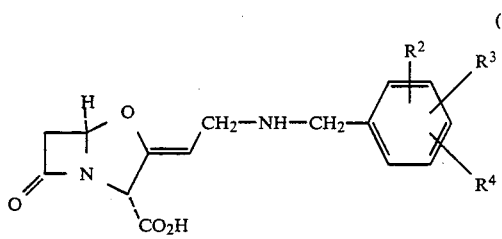

wherein $R^3$ and $R^4$ represent inter alia hydrogen, fluorine, chlorine, $C_{1-3}$alkyl or $C_{1-3}$ alkoxy, and $R^2$ represents inter alia an alkoxycarbonyl group containing 1–3 carbon atoms in the alkoxy part.

European Application No. 79301618.9 discloses inter alia compounds of formula (IA):

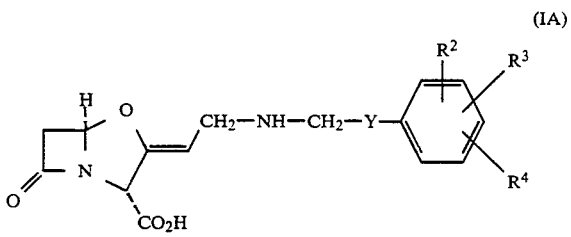

wherein $R^2$, $R^3$ and $R^4$ are as defined above.

The present invention provides the compounds of the formula (II):

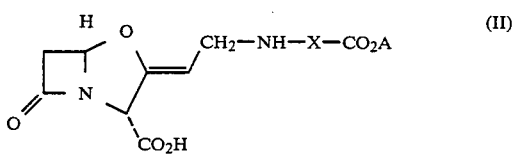

or a pharmaceutically acceptable salt or ester thereof wherein A is a hydrogen atom or an esterifying radical; X is an alkyl group of 1–12 carbon atoms optionally substituted by a hydroxy, amino, acylamino or $C_{1-6}$ alkoxy group, which substituents are not on the carbon atom adjacent to the nitrogen atom; or a $C_{5-7}$ cycloalkyl group; or a phenylalkyl group wherein the carbon atom content of the alkyl part is 1–6 and the phenyl part is optionally substituted with a fluorine, bromine, chlorine, $C_{1-6}$ alkyl, or $C_{1-6}$ alkoxy; with the proviso that when X represents an optionally substituted phenylalkyl group and A represents $C_{1-3}$ alkyl, then the —$CO_2A$ group is attached to the alkyl part of the phenylalkyl group.

Suitably X is a $C_{1-12}$ alkyl group optionally substituted with a hydroxy, amino, acylamino or $C_{1-6}$ alkoxy group which substituents are not on the carbon atom adjacent to the nitrogen atom; or a $C_{5-7}$ cycloalkyl group.

The group X may be an optionally substituted alkyl group such as methyl, ethyl, propyl, butyl, pentyl, hexyl, heptyl, decyl, hydroxyethyl, hydroxypropyl, hydroxybutyl, methoxyethyl, methoxypropyl, ethoxyethyl, propoxyethyl, aminopentyl. A preferred cyclohexyl group is cyclohexyl. Preferably X is $C_{1-6}$ alkyl.

When the group X is optionally substituted phenylalkyl, the group —$CO_2A$ may be attached either to the phenyl part or the alkyl part. Suitable such groups include benzyl, phenylethyl, phenylpropyl, phenylbutyl, fluorobenzyl, chlorobenzyl, bromobenzyl, methylbenzyl, ethylbenzyl, methoxybenzyl, ethoxybenzyl or hydroxybenzyl.

Suitable acylamino groups as substituents for the alkyl group include formyl, $C_{1-6}$ alkanoyl, such as acetyl, and halo($C_{1-6}$)alkanoyl such as trifluoroacetyl.

For example X may represent a methyl, ethyl, propyl, butyl, pentyl, hexyl, heptyl, hydroxyethyl, hydroxypropyl or cyclohexyl group.

Alternatively X may represent a benzyl, bromobenzyl, chlorobenzyl, fluorobenzyl, methylbenzyl, methoxybenzyl or hydroxybenzyl group.

More suitably X is a phenylethyl, phenylpropyl or phenylbutyl group.

Preferred groups X include the ethyl, propyl, butyl and benzyl groups.

A particularly preferred group X is ethyl.

A further particularly preferred group X is benzyl.

It is realised that there are two carboxylate groups in the compounds of the formula (II), thus the compounds of this invention may be presented in the form of a di-ester. Alternatively the compounds of the formula (II) may have one carboxylate function esterified and the other salified. In a further form the compounds of the formula (II) may be presented as di-salts. It is to be realised also that reference to a salt hereinabove covers the compounds of the formula (II) when in zwitterionic form.

In a preferred aspect of this invention the compounds of the formula (II) are presented in the form of a zwitterion wherein A is a hydrogen atom or an esterifying radical.

In a further preferred aspect of this invention the compounds of the formula (II) are presented in the form of a mono-ester wherein A is a hydrogen atom or a salting group.

In a further preferred aspect of this invention the compounds of the formula (II) are presented in the form of a di-salt.

Suitable pharmaceutically acceptable salting groups that may be present in a compound of this invention include the sodium, potassium and calcium ions.

Preferably the pharmaceutically acceptable salting group present in a compound of this invention is either a sodium or potassium ion.

Certain suitable derivatives of the compounds of the formula (II) include those of the formula (III):

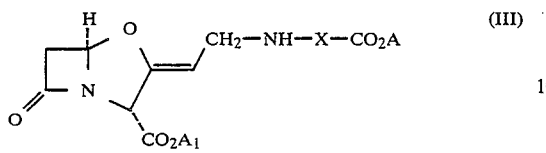

wherein A is a hydrogen atom, or an alkyl group of 1–6 carbon atoms optionally substituted by an alkoxy or acyloxy group of 1–7 carbon atoms, or is a group of the sub-formula (b):

$$CHA_2A_3 \qquad (b)$$

wherein $A_2$ is an alkenyl or alkynyl group of up to 5 carbon atoms or is a phenyl group optionally substituted by a fluorine, chlorine, bromine, nitro or alkyl or alkoxyl of up to 4 carbon atoms; and $A_3$ is a hydrogen atom, an alkyl group of up to 4 carbon atoms or a phenyl group optionally substituted by a fluorine, chlorine, bromine, nitro or alkyl or alkoxyl of up to 4 carbon atoms; and $A_1$ is as defined for A hereinabove.

Suitable values for A or $A_1$ include a hydrogen atom and the methyl, ethyl, n-propyl, n-butyl, allyl, $CH_2\text{---}C\!\equiv\!CH$, methoxymethyl, acetoxymethyl, propionoxymethyl, pivaloyloxymethyl, ethoxycarbonyloxymethyl, methoxycarbonyloxyethyl, ethoxycarbonyloxyethyl, dimethoxyphthalidyl, benzyl, methoxybenzyl, ethoxybenzyl, nitrobenzyl and chlorobenzyl groups.

Certain favoured values A or $A_1$ include a hydrogen atom and the methyl, ethyl, propyl, methoxy; methyl, acetoxymethyl, acetoxyethyl, phthalidyl, ethoxycarbonyloxymethyl, and α-ethoxycarbonyloxyethyl groups.

Certain favoured groups $A_2$ include the phenyl and 4-methoxyphenyl groups. A particularly favoured moiety $A_3$ is the hydrogen atom.

Certain other favoured values for A or $A_1$ include those of the sub-formulae (c), (d) and (e):

$$-CHA_5-OA_6 \qquad (c)$$

$$-CHA_5-COA_6 \qquad (d)$$

$$-CHA_5-CO_2A_6 \qquad (e)$$

wherein $A_5$ is a hydrogen atom or a methyl group and $A_6$ is an alkyl group of up to 4 carbon atoms or a phenyl or benzyl group either of which may be substituted by one or two alkyl or alkoxyl groups of up to 3 carbon atoms or by a fluorine, chlorine or bromine atom or a nitro group; or $A_5$ is joined to $A_6$ to form the residue of an unsubstituted saturated 5- or 6-membered heteroalicyclic ring or an orthophenylene group which may be substituted by one or two alkyl or alkoxyl groups of up to 3 carbon atoms or by a fluorine, chlorine or bromine atom or nitro group.

An apt acyclic value for the sub-group of the formula (c) is $-CH_2-OA_6$.

An apt acyclic value for the sub-group of the formula (d) is $-CH_2-CO-A_6$.

An apt acyclic value for the sub-group of the formula (e) is $-CH_2-CO_2A_6$.

A further apt acyclic value for the sub-group of the formula (e) is $-CH(CH_3)-CO_2A_6$.

Favoured values for $A_6$ in the preceding acyclic moieties include the methyl, ethyl, propyl, butyl, phenyl and benzyl groups.

Apt cyclic values for the sub-group of the formula (d) include the tetrahydropyranyl and tetrahydrofuranyl groups.

Di-esters of the compounds of the formula (II) may be presented in the form of their acid addition salts if desired. The acid used to form the salt will most suitably be pharmaceutically acceptable, but non-pharmaceutically acceptable acid addition salts are also envisaged, for example as intermediates in the preparation of the pharmaceutically acceptable salts by ion exchange. Suitable pharmaceutically acceptable acid addition salts include those of inorganic and organic acids, such as hydrochloric, phosphoric, sulphuric, methanesulphonic, toluenesulphonic, citric, malic, acetic, lactic, tartaric, propionic, succinic or the like acid. Most suitably the acid addition salt is provided as a solid and preferably as a crystalline solid.

An especially suitable form of the compounds of the formula (III) is that in which A is a hydrogen atom or an esterifying radical and $A_1$ is a hydrogen atom.

Compounds when in this form tend to exist as zwitterions, and are preferred aspects of this invention.

Compounds of the formula (III) when in zwitterionic form tend to be crystalline, and as such are especially preferred aspects of this invention.

Compounds of this invention when in crystalline form may be solvated, for example hydrated.

The present invention provides a pharmaceutical composition which comprises a compound of this invention and a pharmaceutically acceptable carrier.

The compositions of the invention include those in a form adapted for oral, topical or parenteral use and may be used for the treatment of the infection in mammals including humans.

Suitable forms of the compositions of this invention include tablets, capsules, creams, syrups, suspensions, solutions, reconstitutable powders and sterile forms suitable for injection or infusion. Such compositions may contain conventional pharmaceutically acceptable materials such as diluents, binders, colours, flavours, preservatives, disintegrant and the like in accordance with conventional pharmaceutical practice in the manner well understood by those skilled in the art of formulating antibiotics.

Injectable or infusable compositions of a compound of the invention are particularly suitable as high blood levels of the compound can occur after administration by injection or infusion. Thus, one preferred composition aspect of this invention comprises a compound of the invention in sterile form and most suitably in sterile crystalline form. The zwitterionic compounds of this invention are particularly suitable for use in such compositions.

The injectable solution of the compound of this invention may be made up in a sterile pyrogen-free liquid such as water, aqueous ethanol or the like.

An alternative approach to administering the compounds of this invention and especially those zwitterionic compounds of the formula (II) is to utilise an injectable suspension. Such suspensions may be made up in sterile water; sterile saline or the like and may also contain suspending agents such as polyvinylpyrrolidone, lecithin or the like (for example in the manner described for amoxycillin trihydrate in Belgian Pat. No. 839109). Alternatively such compositions may be prepared in an acceptable oil suspending agent such as arachis oil or its equivalent. The use of suspensions can give rise to advantageously prolonged blood levels of the medicament. Belgian Pat. No. 839109 may be consulted for suitable methods and materials for producing injectable aqueous suspensions. For use in such suspensions the zwitterionic compound of this invention should be in the form of fine particles as described in said Belgian Patent.

Unit dose compositions comprising a compound of this invention adapted for oral administration form a further suitable composition aspect of this invention.

Unit dose compositions comprising a compound of this invention adapted for topical administration are also presented by this invention. In this instance 'topical administration' also includes local administration to internal surfaces of mammary glands of cattle, for example during the treatment of mastitis by intra-mammary administration.

The compound of the formula may be present in the composition as sole therapeutic agent or it may be present together with other therapeutic agents such as a penicillin or cephalosporin. Considerable advantages accrue from the inclusion of a penicillin or cephalosporin since the resulting composition shows enhanced effectiveness (synergy).

Suitable penicillins for inclusion in the compositions of this invention include benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbenicillin, and other known penicillins including pro-drugs therefore such as their in vivo hydrolysable esters such as the acetoxymethyl, pivaloyloxymethyl, α-ethoxycarbonyloxyethyl or phthalidyl esters of ampicillin, benzylpenicillin or amoxycillin, and aldehyde or ketone adducts of penicillins containing a 6-α-aminoacetamide side chain (such as hetacillin, metampicillin and analogous derivatives of amoxycillin) or α-esters of carbenicillin or ticarcillin such as their phenyl or indanyl α-esters.

Suitable cephalosporins for inclusion in the compositions of this invention include cefatrizine, cephaloridine, cephalothin, cefazolin, cephalexin, cephacetrile, cephamandole nafate, cephapirin, cephradine, 4-hydroxycephalexin, cefaparole, cephaloglycin, and other known cephalosporins or prodrugs thereof.

Such compounds are frequently used in the form of a salt or hydrate of the like.

Naturally if the penicillin or cephalosporin present in the composition is not suitable for oral administration then the composition will be adapted for parenteral administration.

Highly favoured penicillins for use in the compositions of this invention include ampicillin, amoxycillin, carbenicillin and ticarcillin. Such penicillins may be used as a pharmaceutically acceptable salt such as the sodium salt. Alternatively the ampicillin or amoxycillin may be used in the form of fine particles of the zwitterionic form (generally as ampicillin trihydrate or amoxycillin trihydrate) for use in an injectable suspension, for example, in the manner hereinbefore described for a compound of this invention.

The preferred penicillin for use in the synergistic composition is amoxycillin, for example as its sodium salt or trihydrate.

Particularly suitable cephalosporins for use in the compositions of this invention include cephaloridine and cefazolin which may be in the form of a pharmaceutically acceptable salt for example the sodium salt.

When present together with a cephalosporin or penicillin, the ratio of a compound of the invention to the penicillin or cephalosporin agent may vary over a wide range of ratios, such as from 10:1 to 1:10 for example about 3:1, 2:1, 1:1, 1:2, 1:3, 1:4, 1:5 or 1:6, (wt/wt, based on pure free antibiotic equivalent). Orally adminstrable compositions containing a compound of the invention will normally contain relatively more synergist than corresponding injectable compositions.

The total quantity of a compound of the invention in any unit dosage form will normally be between 25 and 1000 mg and will usually be between 50 and 500 mg, for example about 62.5, 100, 125, 150, 200 or 250 mg.

Compositions of this invention may be used for the treatment of infections of inter alia, the respiratory tract, the urinary tract and soft tissues in humans and mastitis in cattle.

Normally between 50 and 1000 mg of the compounds of the invention will be administered each day of treatment but more usually between 100 and 750 mg of the compounds of the invention will be administered per day, for example at 1–6 doses, more usually as 2, 3 or 4 doses.

The penicillin or cephalosporin in the synergistic composition of this invention will normally be present at approximately the amount at which it is conveniently used which will usually be expected to be from about 62.5 to 1000 mg per dose, more usually about 125, 250 or 500 mg per dose.

One particularly favoured composition of this invention will contain from 150 to 1000 mg of amoxycillin as the trihydrate or sodium salt and from 25 to 500 mg of a compound of this invention.

Most suitably this form of composition will contain a compound of the formula (II) when in crystalline zwitterionic form.

A further particularly favoured composition of this invention will contain from 150 to 1000 mg of ampicillin or a pro-drug therefore and from 25 to 500 mg of a compound of this invention.

Most suitably this form of composition will contain ampicillin trihydrate, ampicillin anhydrate, sodium ampicillin, hetacillin, pivampicillinhydrochloride, bacampicillin hydrochloride, or talampicillin hydrochloride. Most suitably this form of the composition will contain a compound of the formula (II) when in crystalline zwitterionic form.

Most suitably the preceding composition will contain from 200 to 700 mg of the penicillin component. Most suitably the preceding composition will comprise from 50 to 250 mg of a compound of the formula (II) preferably in crystalline zwitterionic form.

Such compositions may be adapted for oral or parenteral use except when containing an in vivo hydrolysable ester of ampicillin or amoxycillin in which case the compositions will not be adapted for parenteral administration.

Another particularly favoured composition of this invention will contain from 200 to 2000 mg of carbenicillin, ticarcillin or a pro-drug therefore and from 50 to 500 mg of a compound of the invention.

Suitably this form of composition will contain di-sodium carbenicillin. Suitably this form of the composition will contain di-sodium ticarcillin.

More suitably this form of the composition will contain from 75 to 250 mg of a compound of the formula (II) preferably in crystalline zwitterionic form. Such compositions containing di-salts of carbenicillin and ticarcillin will be adapted for parenteral administration.

The present invention also provides a method of treating bacterial infections in humans or domestic mammals which comprises the administration of a composition of this invention.

Commonly the infection treated will be due to a strain of *Staphylococcus aureus, Klebsiella aerogenes, Escherichia coli, Proteus sp.* or the like. The organisms believed to be most readily treated by an antibacterially effective amount of a compound of this invention is *Staphylococcus aureus*. The other organisms named are more readily treated by using a synergistically effective amount of the compound of the invention and a penicillin or cephalosporin. The administration of the two components may take place separately but in general we prefer to use a composition containing both the synergist and the penicillin or cephalosporin.

The indications for treatment include respiratory tract and urinary tract infections in humans and mastitis in cattle.

The present invention also provides a process for the preparation of a compound of formula (II) or a pharmaceutically acceptable salt or ester thereof which process comprises reacting a compound of formula (IV) or (V), or an ester thereof:

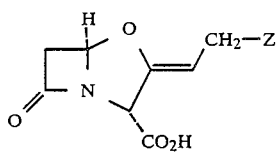

(IV)

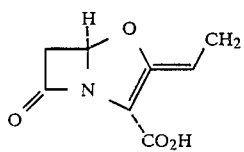

(V)

wherein 2 is a displaceable group; with an amine of formula (VI):

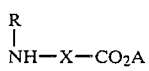

(VI)

wherein A and X are as defined with respect to formula (II) and R is a removable protecting group; and thereafter removing the group R.

Suitable groups Z include halogen, for example chlorine or bromine, alkyl- or aryl-sulphonyloxy, or acyloxy such as optionally substituted $C_{1-6}$ alkanoyloxy for example acetoxy or dichloroacetoxy.

Suitably the reaction of the amine of the formula (VI) with the compound of the formula (IV) or (V) will take place in an aprotic solvent such as acetonitrile or dimethylformamide at a non-extreme temperature, for example $-10°$ to $+50°$, more usually $-5°$ to $+25°$, and conveniently within the range $0°$ to $+20°$.

Suitably the group R is one which may be removed by hydrogenation. For example R may be a group of the sub-formula (f):

$$-CH_2CR_7=CHR_8 \qquad (f)$$

wherein $R_7$ is a hydrogen atom or lower alkyl group and $R_8$ is a hydrogen atom, a lower alkyl group, or a phenyl group optionally substituted with a lower alkyl or lower alkoxy group; or $R_7$ and $R_8$ together represent a butadiene moiety.

Particularly suitable groups R include the following:
$CH_2CH=CH_3$, $CH_2CH=CHC_6H_5$,
$CH_2C(CH_3)=CH_2$, $CH_2C(C_2H_5)=CH_2$,
$CH_2C(nC_3H_7)=CH_2$, $CH_2C(CH_3)=CHCH_3$,
$CH_2C(CH_3)=C(CH_3)_2$, $CH_2C(CH_3)=CHC_2H_5$,
$CH_2C(CH_3)=CHC_6H_5$ and $CH_2C_6H_5$.

Favoured groups R are $CH_2CH=CHCH_3$, $CH_2CH=CHC_6H_5$, $CH_2C(CH_3)=CH_2$, $CH_2C(CH_3)=CHC_6H_5$ and $CH_2C_6H_5$.

Particularly preferred groups R are $CH_2C(CH_3)=CH_2$, $CH_2C(CH_3)=CHC_6H_5$ and $CH_2C_6H_5$.

The group A and the ester group of compounds (IV) and (V) may be groups that can be removed after the reaction, for example by hydrogenation, or alternatively the ester groups may be left intact after the reaction. Thus four forms of compounds of this invention may be presented: (a) di-salts, (b) di-esters, (c) a mono-ester wherein group A is a hydrogen atom or a salifying group, and (d) a mono-ester wherein group A is the esterifying radical.

The hydrogenation is normally carried out in the presence of a transition metal catalyst.

The catalyst we have preferred to use is palladium, for example in the form of palladium on carbon (charcoal), palladium on barium sulphate, palladium on calcium carbonate, palladium black or the like.

A favoured catalyst is palladium on carbon (sometimes referred to as palladium on charcoal); for example 5%, 10%, 20% or 30% palladium on carbon.

A low, medium or high pressure of hydrogen may be used in this reaction, for example from 1 to 6 atmospheres.

The reaction is normally carried out at a non-extreme temperature, for example from $0°-30°$ and more usually from $12°-25°$. It is generally convenient to carry out the reaction at ambient temperature.

Suitably solvents for carrying out the hydrogenation include ethanol, n-propanol, isopropanol, tetrahydrofuran, dioxan, ethyl acetate or mixtures of such solvents or such solvents in the presence of water. A favoured solvent is ethanol.

Favoured hydrogenolysable esters include benzyl and substituted benzyl esters such as methoxybenzyl, nitrobenzyl (for example the p-nitrobenzyl ester), chlorobenzyl and bromobenzyl esters. A particularly suitable hydrogenolysable ester is the benzyl ester. A further particularly suitable hydrogenolysable ester is the p-methoxybenzyl ester.

The product may generally be isolated from the reaction mixture by filtering off the solids (the catalyst which should be well washed to remove the product) and then evaporating the solvent, preferably under low pressure, to yield the initial product. Further purification may be effected by such conventional methods as chromatography over cellulose or other mild stationary phase eluting with a $C_{1-4}$ alkanol optionally in the presence of water and optionally in the presence of tetrahydrofuran. Evaporation of the combined active fraction (identified by aqueous potassium permanganate spray on tlc) then yields the desired compound in pure form. The desired product is normally obtained in crystalline form (unless it is an unsalted ester). Trituration under ethanol, isopropanol or the like $C_{1-4}$ alkanol or other conventional solvent such as a ketone, either or ester solvent or other conventional solvent (for example of up to 6 carbon atoms and more suitably of up to 4 carbon atoms) may also be used to aid crystallization. Recrystallization from ethanol or the like may also be employed. The solvent used in such processes may advantageously be moist.

Unsalted esters of the compounds of the formula (II) tend to be oils so that it is often more convenient for handling to convert them into solid acid addition salts, for example by reaction with one equivalent of an acid.

The foregoing process is not preferred when preparing compounds of the formula (II) in which number of carbon atoms in the chain directly linking the —NH— group and the —$CO_2A$ group is one.

In an improved process for the preparation of compounds of the formula (II) wherein the number of carbon atoms in the chain directly linking the —NH— group and the $CO_2A$ group is one, the present invention provides a process which comprises the reduction with a complex hydride of a salt of a compound of the formula (VII):

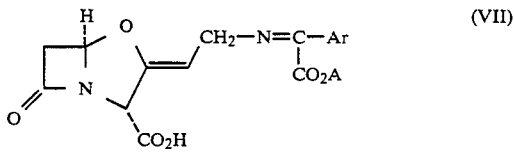

(VII)

wherein Ar is a phenyl group optionally substituted by a bromine, fluorine or chlorine atom or an alkyl group of 1-3 carbon atoms or an alkoxy group of 1-3 carbon atoms and A is as defined in relation to formula (II).

Most suitably the complex hydride is a water soluble complex hydride.

Suitable water soluble complex hydrides include borohydrides such as lithium borohydride, sodium borohydride, potassium borohydride or the like. In general an excess of the hydride is employed.

Suitably the reaction is carried out in an aqueous medium, for example in water or in a mixture of water with an inert water miscible organic solvent such as tetrahydrofuran, dioxan or the like.

It is a favoured feature of this invention that ambient and near ambient temperatures may be employed, for example the reaction may be carried out at a temperature of from 0°-30° and conveniently at ambient, for example at about 18°-25°.

The pH of the reaction is best kept below 10 and this may be effected by the addition of an acid such as hydrochloric or like mineral acid simultaneously with the complex hydride. This may be carried out in a pH-stat or other similar system.

Once the reaction is over it is advantageous to return the pH to about 5-8.

The desired product may be obtained from the reaction mixture by evaporation of the solvent. Purification may be effected by crystallisation (for example before all the solvent has been evaporated off) or by column chromatography, for example using silica gel or cellulose and butanol/ethanol/water 4/4/1.

The compounds of the formula (VII) are novel and as such form an aspect of this invention.

The present invention also provides a process for the preparation of a compound of the formula (VII) which process comprises the reaction of 9-aminodeoxyclavulanic acid with a compound of the formula (VIII):

$$ArCOCO_2A \qquad (VIII)$$

wherein Ar is as defined in relation to formula (VII) and A is as defined in relation to formula (II) in an aqueous solvent wherein the solution is maintained at an alkaline pH.

The pH of the solution is most suitably maintained in the region of 7-10 and preferably 8-9. This may be effected by the addition of base such as an alkali or alkaline earth metal hydroxide, a carbonate of bicarbonate or with a strong organic base which is unreactive towards aldehydes. Thus suitable bases include lithium hydroxide, sodium hydroxide, potassium hydroxide, calcium hydroxide, barium hydroxide, sodium carbonate, potassium bicarbonate, triethylamine and the like. It is convenient to add the base automatically, for example in a pH-stat.

The present invention also provides a process for the preparation of an ester of a compound of the formula (II) which process comprises the reaction of the compound of the formula (II) with an esterifying agent.

The zwitterionic compound of the formula (II) may be dissolved or suspended in a solvent such as dimethylformamide, hexamethylphosphoramide, dichloromethane, ethyl acetate or other non-esterifiable solvents and therein esterified. Suitable temperatures for such a reaction range from about 0° to about 25°. Suitable esterifying reagents include reactive halides and their equivalents, alkyl oxonium salts and the like.

When a reagent such as a reactive iodide, chloride, bromide, tosylate, mesylate or the equivalent is used, the resulting salt is generally suitable for use in a composition of this invention. Alternatively, the salt may be converted to a free base or alternative salt. When an alkyl oxonium salt is used, it is preferred to convert the resulting tetrafluoroborate to the free base or alternative salt. The various aforementioned salts may be converted to the free base by neutralisation, for example by contacting a solution of the salt in water with an organic phase, neutralising the salt by adding a base and extracting the liberated amine into the organic phase. This amine may thereafter be re-salted by reacting with an appropriate acid, for example in a dry organic solvent. It is generally preferred to use not more than one equivalent of acid for this process. Alternatively the originally formed salt may be converted into the alternative salt using an ion exchange material, for example, by passing an aqueous solution of one salt through a bed of an anion exchange resin in the form of the desired salt such as the chloride form.

The salts may normally be obtained in solid form by dissolving in a fairly polar organic solvent (such as ethanol, tetrahydrofuran or the like) and then precipitating using a non-polar solvent such as diethyl ether, cyclohexane or the like.

The salts of the esters of the compounds of the formula (II) may normally be obtained in crystalline form by conventional methods such as trituration under (or crystallisation or recrystallisation from) a suitable organic solvent such as ether, acetone, acetonitrile, tetrahydrofuran or the like.

The present invention also provides a process for the preparation of an ester of the compound of the formula (II) which process comprises the reaction of an acid addition salt of the compound of the formula (II) with an alcohol in the presence of a condensation promoting agent.

Suitable condensation promoting agents for use in this process include carbodiimides such as dicyclohexylcarbodiimide and the chemical equivalents thereof.

The acid addition salt may be formed in situ or may be preformed. The acid employed will normally be a strong acid such as a methane sulphonic acid, p-toluene sulphonic acid or the like or trifluoroacetic acid or the like.

The reaction is normally carried out in an inert organic solvent. When the ester being formed is that of a liquid alcohol it is convenient to use that alcohol as the solvent or as part of the solvent system. The esterification is generally performed at a no-extreme temperature such as 0°–35°, for example from about 10°–25° C. Conveniently the reaction mixture may be performed at ambient temperature.

Other methods of preparing esters of the compounds of the formula (II) are those described in the aforementioned patents and applications which are incorporated herein by reference.

In a further aspect this invention also provides a process for the preparation of compounds of formula (II) which process comprises reacting a compound of formula (IX) or an ester thereof:

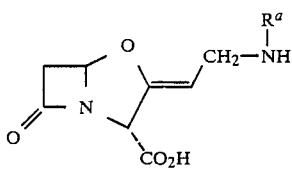

where $R^a$ represents hydrogen or a removable protecting group; with a compound of formula (X):

$$Z^a-X-CO_2A \qquad (X)$$

wherein X and A are as defined with respect to formula (II) and $Z^a$ is a readily displaceable group; and thereafter removing any group $R^a$ which is not hydrogen.

When the group $R^a$ is not hydrogen it may conveniently be any of the groups R defined above with respect to formula (VI).

Suitable groups $Z^a$ include halogen, alkyl- or aryl-sulphonyloxy, such as methanesulphonyloxy, benzenesulphonyloxy, p-toluenesulphonyloxy, p-bromobenzenesulphonyloxy. A preferred group $Z^a$ is iodine. When X is CH$_2$, $Z^a$ is suitably bromine.

The reaction of compound (IX) with compound (X) is conveniently carried out in an inert organic solvent such as dimethylformamide, acetonitrile or methylene dichloride, preferably in the presence of a strong non-nucleophilic organic base, and at a non-extreme temperature for example −10° to +50°, more usually −5° to +20° and conveniently in the range −5° to +10°.

The foregoing process is not preferred when preparing compounds of formula (II) in which X represents —CH$_2$—CH$_2$—.

The following Examples illustrate the preparation of compounds of this invention.

EXAMPLE 1

(a) Benzyl 9-N-[2'-(benzyloxycarbonyl)ethyl]-N-(2''-methyl-3''-phenylallyl)aminodeoxyclavulanate Benzyl dichloroacetylclavulanate (1.01 g: 2.53 mM) in dry dimethylformamide (30 cm$^3$) at −15° was treated with 1.9 equivalents of N-[2-(benzyloxycarbonyl)ethyl]-N-(2'-methyl-3'-phenylallyl)amine and stirred at −15° to 0° over 2 hours. The mixture was poured into ethyl acetate (300 cm$^3$), washed with water (5×100 cm$^3$), saturated brine (5×100 cm$^3$), dried (anhydrous magnesium sulphate) and evaporated to an oil. This oil was chromatographed on silica eluting with methyl acetate:-cyclohexane (1:2). Fractions were collected containing the title compound Rf (SiO$_2$/ethyl acetate:cyclohexane (1:1)=0.83 (detection by aqueous potassium permanganate spray), combined fractions were evaporated to yield 0.52 g of an oil (35%). (film) 1805, 1740, 1700, 1305, 1180, 1015, 755, 700 cm$^{-1}$; (CDCl$_3$) 1.78 (3H, s), 2.35–2.80 (4H, m), 2.93 (1H, d, J 17 Hz), 2.96 (2H, s), 3.18 (2H, d, J 7 Hz), 3.37 (1H, dd, J 17 and 3 Hz), 4.69 (1H, 6, J 7 Hz), 5.08 (3H, broad s), 5.16 (2H, s), 5.60 (1H, broad d, J 3 Hz), 6.34 (1H, broad s), 7.23 (5H) and 7.30 (10H) (2×s).

(b) 9-N-(2'-Carboxyethyl)aminodeoxyclavulanic acid

Benzyl 9-N-[2'-(benzyloxycarbonyl)ethyl]-N-(2''-methyl-3''-phenylallyl)aminodeoxyclavulanate (134 mg: 0.23 mM) in ethanol:tetrahydrofuran (15 cm$^3$; 1:1) was hydrogenolysed at atmospheric pressure in the presence of 10% palladium on carbon (45 mg, prehydrogenated for 15 minutes) for 20 minutes, when water (3 cm$^3$) was added and hydrogenolysis continued for 1 hour. The catalyst was filtered off and washed with ethanol (20 cm$^3$). The filtrate was evaporated to an oil, on addition of methanol crystals formed which were filtered off cold and washed with a little cold methanol. Drying in vacuo afforded the title compound as a white crystalline solid, yield=26 mg (42%), rF (SiO$_2$/butanol:propan-2-ol:water; 7:7:6)=0.38.

(Nujol) (3700–2000), (1850–1795), 1720, 1700, 1612, 1580, 1305, 1230, 1190, 1122, 1075, 1045, 1020, 1005, 995, 920, 895, 805, 785, 755 cm$^{-1}$; (KBr) (3700–3250), (3250–2890), (2890–2500), (2500–2200), 1790 broad, 1715 broad, 1575 very broad), 1400, 1300, 1190, 1118, 1082, 1070, 1045, 1015, 915, 895, 795, 758 cm$^{-1}$; (D$_2$O) 2.5502.87 (2H, m), 3.10 (1H, d, J 17 Hz), 3.05–3.38 (2H, m), 3.58 (1H, dd, J 17 and 3 Hz), 3.75 (2H, d, J 7 Hz), 4.81 (1H, dt, J 7 Hz and 1.25 Hz), 5.03 (1H, broad s), 5.75 (1H, d, J 3 Hz).

EXAMPLE 2

(a) Benzyl 9-N-[2'(benzyloxycarbonyl)ethyl]-N-(2''-Methylallyl)-aminodeoxyclavulanate Benzyl dichloroacetylclavulanate (0.98 g: 2.45 mM) in dry dimethylformamide (50 cm$^3$) at −10° was treated with 1.9 equivalents of N-[(2-benzyloxycarbonyl)ethyl]-N-(2'-methylallyl)amine with stirring. The mixture was stirred from −10° to 0° over 1 hour then at 0° for 1½ hours. The mixture was poured into ethyl acetate (250 cm$^3$), washed with water (6×100 cm$^3$) saturated brine (6×150 cm$^3$), dried (anhydrous magnesium sulphate) and evaporated to an oil. This oil was chromatographed on silica eluting with ethyl acetate:cyclohexane (1:3). Fractions were collected containing the title compound and the combined fractions were evaporated to yield the title compound as an oil (250 mg) (20%), (film) 1802, 1740, 1700, 740, 700 cm$^{-1}$.

(b) 9-N-(2'-Carboxyethyl)aminodeoxyclavulanic acid

Benzyl 9-N-[(2'-benzyloxycarbonyl)ethyl]-N-(2''-methylallyl)aminodeoxyclavulanate (0.23 g; 0.45 mM) in tetrahydrofuran:ethanol (1:2; 25. cm$^3$) was hydrogenolysed in the presence of 10% palladium on carbon (90 mg; which had been prehydrogenated for 15 minutes) for 15 minutes when water (3 cm$^3$) was added and hydrogenolysis continued for $\frac{3}{4}$ hour. The catalyst was filtered off and washed with aqueous ethanol (20 cm$^3$), the clear filtrate was evaporated and methanol (5 cm$^3$) added, the resulting crystals were filtered off (0° C.) and washed with cold methanol, drying afforded 27 mg (22%) of the title compound as a white crystalline solid, Ff (SiO$_2$/ethanol:water:ethyl acetate; 2:2:5)=0.26. (Nujol) (3700–2200) very broad 1800, 1720, 1695, 1605, 1575, 1300, 1227, 1187, 1042, 1015, 915, 892 cm$^{-1}$. The proton magnetic resonance spectrum was consistent with the required product.

EXAMPLE 3

(a) N-[4-(Benzyloxycarbonyl)butyl]-N-(2-methyl-3-phenylallyl)amine 13.7 g (36 mM) of 4-(benzyloxycarbonyl)butylamine para toluene sulphonate salt was stirred vigorously in ethyl acetate—water whilst being treated with aqueous sodium hydroxide to pH 9.5. The organic phase was washed with saturated brine, dried (anhydrous magnesium sulphate), benzyl alcohol (100 cm$^3$) added, and the ethyl acetate evaporated. The solution was treated with one equivalent of α-methylcinnamaldehyde and stirred for $\frac{1}{2}$ hour. Dichloromethane (50 cm$^3$) was added and the reaction mixture treated with excess sodium borohydride. The mixture was filtered and the filtrate diluted with dichloromethane (100 cm$^3$), washed with saturated brine (4×150 cm$^3$) and dried (anhydrous magnesium sulphate). The dichloromethane was removed by evaporation under reduced pressure and the residue diluted with diethyl ether (300 cm$^3$). This solution was treated with excess para toluene sulphonic acid in ether. The resultant crystals were filtered off, washed with ether and dried to yield 2.7 g (15%) of the title compound as a para-toluene sulphonate salt. This salt was extracted into ethyl acetate with aqueous sodium hydroxide (pH 9–10). The organic phase was washed with saturated brine, dried (anhydrous magnesium sulphate) and evaporated to an oil, yield=1.85 g (15%), (film) 3330, 1735, 1450, 1155, 750, 700 cm$^{-1}$; (CDCl$_3$) 1.35-2.00 (5H, m), 1.85 (3H, d, J 1 Hz), 2.37 and 2.62 (4H, 2×t, J 6.5 Hz), 3.27 (2H, s), 5.10 (2H, s), 6.42 (1H, broad s), 7.26 and 7.34 (10H, 2×s).

(b) Benzyl 9-N-[4'-(benzyloxycarbonyl)butyl]-N-(2''-methyl-3''-phenylallyl)aminodeoxyclavulanate Benzyl dichloroacetylclavulanate (10 g; 2.5 mM) in dry dimethylformamide (20 cm$^3$) was treated at −15° with 1.9 equivalent of N-[4-(benzyloxycarbonyl)butyl]-N-(2-methyl-3-phenylallyl)amine, and stirred between −10° and −5° over 1$\frac{1}{2}$ hours. The reaction mixture was poured into ethyl acetate (200 cm$^3$), washed with water (5×150 cm$^3$), saturated brine (5×150 cm$^3$), dried (anhydrous magnesium sulphate) and evaporated in the presence of toluene to a small volume. This crude product was chromatographed on silica eluting with ethyl acetate:cyclohexane (1:3), fractions were collected containing the title compound, Rf (SiO$_2$/ethyl acetate:cyclohexane; 1:2)=0.5 (detection by aqueous potassium permanganate spray). Combined fractions were evaporated to yield the title compound as an oil, 0.21 (14%), (film) 1805, 1740, 1700 (shoulder), 745, 705 cm$^{-1}$.

The proton magnetic resonance spectrum was consistent with the desired product.

(c) 9-N-(4'-Carboxybutyl)aminodeoxyclavulanic acid

Benzyl 9-N-[4'-benzyloxycarbonyl)butyl]-N-(2''-methyl-3''-phenylallyl)aminodeoxyclavulanate (200 mg; 0.33 mM) in ethanol-tetrahydrofuran; 20 cm$^3$ (10:1) plus water ($\frac{1}{2}$ cm$^3$) was hydrogenolysed at atmospheric pressure in the presence of 10% palladium on carbon (80 mg; which had been prehydrogenated for 10 minutes) for 1$\frac{1}{2}$ hours. The catalyst was filtered off and washed with ethanol (20 cm$^3$), then with aqueous ethanol (50 cm$^3$), the aqueous washings were collected separately and were evaporated to afford the title compound as a white solid, this solid was washed with cold methanol and dried to yield 16.4 mg. The ethanolic washings from the catalyst were hydrogenolysed for a further 2$\frac{1}{4}$ hours in the presence of 10% palladium on carbon (50 mg). The catalyst was filtered off and washed with aqueous ethanol (30 cm$^3$), the filtrate was evaporated to an oil, methanol was added (5 cm$^3$) and the solution cooled (0°). The resultant white crystals were filtered off and washed with cold (0°) methanol and dried to afford a further 7.8 mg of the title compound. Total yield=24.2 mg (25%), Rf (SiO$_2$/ethylacetate-ethanol-water; 5:2:2)=0.25, ν (Nujol) 1805, 1725, 1695, 1610, 1585, 1300, 1185, 1045, 1015, 892 cm$^{-1}$; δ (D$_2$O) 1.35-1.85 (4H, m), 2.13-2.50 (2H, m), 2.78-3.1 (2H, m), 3.08 (1H, d, J 17 Hz), 3.55 (1H, dd, J 17 and 3 Hz), 3.68 (2H, d, J 8 Hz), 4.77 (1H, broad t, J 8 Hz), 4.98 (1H, s), 5.73 (1H, d, J 3 Hz).

EXAMPLE 4

(a) N-[4-(Benzyloxycarbonyl)benzyl]-N-(2'-methylallyl)amine 4-(Benzyloxycarbonyl)benzaldehyde (12 g; 50 mM) in benzyl alcohol (70 cm$^3$) was treated with 2-methylallylamine (4.5 cm$^3$; 1 equivalent) and stirred for 3 hours. Dichloromethane (50 cm$^3$) and water (2 cm$^3$) were added followed by excess sodium borohydride. The precipitated solid was filtered off and the filtrate diluted with dichloromethane (200 cm$^3$). This solution was washed with brine (4×200 cm$^3$) and dried (anhydrous magnesium sulphate). The dichloromethane was evaporated and diethyl ether added (300 cm$^3$), to this solution was added para-toluene sulphonic acid in ether until the solution was acidic. The resultant white solid was filtered off, washed with ether and dried to yield 16.3 g of the para-toluene sulphonate salt. This salt was stirred vigorously with water and ethyl acetate whilst being treated with aqueous sodium hydroxide to pH 9.00. The ehthyl acetate phase was washed with water (3×100 cm$^3$), saturated brine (4×100 cm$^3$), dried (anhydrous magnesium sulphate) and evaporated to an oil. This oil was chromatographed on silica eluting with ethyl acetate-cyclohexane (1:3). Fractions were collected containing the title compound and combined fractions were evaporated to yield a viscous oil, 8.69 g (60%), ν (film) 3340 (broad), 1720, 1610, 1450, 1270, 1175, 1095, 1015, 895, 750, 695 cm$^{-1}$; δ (CDCl$_3$) 1.60 (1H, s, exchanges with D$_2$O), 1.78 (3H, s), 3.17 (2H, s), 3.81 (2H, s), 4.93 (2H, broad s), 5.37 (2H, s), 7.29–7.60 (7H, m), 8.10 (2H, d$_{AB}$ J 8 Hz).

Benzyl 9-N-[4'-(benzyloxycarbonyl)benzyl]-N-(2''-methylallyl)-aminodeoxyclavulanate Benzyl dichloroacetylclavulanate (2.73 g; 6.83 mM) in dry dimethylformamide (20 cm$^3$) at 0° was treated with 1.9 equivalents of N-[4-(benzyloxycarbonyl)benzyl]-N-(2'-methylallyl)amine in dimethylformamide (20 cm$^3$) dropwise over ten minutes, then stirred at 0° for 4 hours and allowed to warm up to room temperature over ¾ hour. The mixture was poured into ethyl acetate (250 cm$^3$), washed with water (6×150 cm$^3$), saturated brine (6×150 cm$^3$), dried (MgSO$_4$) and evaporated to an oil. This oil was chromatographed on silica, eluting with ethyl acetate-cyclohexane (1:3). Fractions were collected containing the title compound Rf (SiO$_2$/ethyl acetate-cyclohexane; 1:1)=0.86 (detection by aqueous potassium permanganate spray). Combined fractions were evaporated to an oil, yield=0.8 g (21%), ν (film) 1805, 1750, 1720, 895, 760, 750, 700 cm$^{-1}$; δ(CDCl$_3$) 1.70 (3H, s), 2.85 (2H, s), 6βH obscured, 3.09 (2H, d, J 7 Hz), 3.43 (1H, dd, J 17 and 3 Hz), 3.45 (2H, s), 4.71 (1H, t, J 7 Hz), 4.85 (2H, broad s), 5.05 (1H, s), 5.17 (2H, s), 5.35 (2H, s), 5.60 (1H, d, J 3 Hz), 7.20–7.55 (12H, m), 8.00 (2H, d$_{AB}$ J 8 Hz).

9-N-(4'-Carboxybenzyl)aminodeoxyclavulanic acid

Benzyl 9-N-[4'-(benzyloxycarbonyl)benzyl]-N-(2''-methylallyl)aminodeoxyclavulanate (0.71 g; 1.25 mM), in tetrahydrofuran-ethanol (1:1; 20 cm$^3$) and water (1 cm$^3$) was hydrogenolysed at atmospheric pressure in the presence of 10% palladium on carbon (200 mg) (which had been prehydrogenated for 15 minutes) for 1 hour. The catalyst was filtered off, washed with ethanol (20 cm$^3$), aqueous ethanol (250 cm$^3$) and aqueous isopropanol-tetrahydrofuran (150 cm$^3$) until the filtrate no longer showed any product present by thin layer chromatography. This aqueous washings were collected separately and were evaporated to give a white crystalline solid. This solid was washed with ethanol and dried to yield 183 mg of the title compound, Rf (SiO$_2$/ethylacetate-ethanol-water; 5:2:2)=0.32 (detection by aqueous potassium permanganate spray). ν (Nujol) 1805, 1690, 1602, 1578, 1298, 1275, 1185, 1122, 1150, 1118, 990, 945, 890, 860, 755, 705 cm$^{-1}$; ν (KBr) (3700–2200, broad multiple peaks), 1808, 1690, 1600, 1580, 1465, 1404, 1300, 1275, 1187, 1127, 1055, 1022, 993, 947, 895, 867, 760, 712 cm$^{-1}$; δ (D$_2$O/pyridine d-5) 3.15 (1H, d, J 17 Hz), 3.80 (1H, broad d, J 17 Hz), 4.07 (2H, J 8 Hz), 4.58 (2H, s), 8CH and 3CH obscured by HOD, 6.20 (1H, broad s), 7.85 (2H̄, d$_{AB}$, J̄ 8 Hz), 8.45 (2H, d$_{AB}$, J 8 Hz).

EXAMPLE 5

9-(DL-α-Carboxybenzylamino)deoxyclavulanic acid

A solution consisting 9-aminodeoxyclavulanic acid (0.2 g) and methyl benzoylformate (0.8 g) in water (10 ml) and tetrahydrofuran (15 ml) was stirred and maintained at pH 8–9 by the automatic addition of 1M LiOH solution. Uptake of LiOH solution was continuous, and was allowed to exceed the amount required for Schiff's base formation by a considerable amount (∼2 fold). Sodium borohydride (0.15 g) was then added concurrently with HCl to keep the pH below 9. Once the addition was complete the reaction mixture was brought to pH 7 by the addition of dilute HCl. The reaction mixture was evaporated to dryness and extracted with ethyl acetate. The insoluble residue was re-evaporated with 1.5 ml water, then subjected to column chromatography on silica gel using n-butanol-ethanol-water 7:7:6 v/v elution solvent. Fractions containing the desired product were combined and evaporated to dryness in vacuo. The residue was extracted twice with small volumes of acetone, then with ether and finally dried in vacuo, to yield the product as a pale buff solid; ν (Nujol) 2500–3700 (broad) 1785, 1700, and 1620 cm$^{-1}$ (broad) δ (D$_2$O) 3.20 (1H, d, J 17 Hz), 3.66 (1H, dd, J 17 and 3 Hz), 3.74 (2H, d, J 8 Hz), (HOD at 4.7 obscured many peaks) 5.85 (1H, d, J 3 Hz), and 7.50 (5H, s).

Tlc ran in the elution solvent above showed the product to be quite distinct from 9-aminodeoxyclavulanic acid.

EXAMPLE 6

(a) Benzyl 9-N-(2'-methoxycarbonylethyl)-N-benzylaminodeoxyclavulanate

Benzyl 9-O-dichloroacetylclavulanate (5.3 g; 13.3 mmol), in dry dimethylformamide (70 cm$^3$) at −15° C. was treated dropwise with N-benzyl-O-methyl-β-alanine (1.9 equivalents) in dimethylformamide (20 cm$^3$). The reaction mixture was stirred between −10° and +10° over 1½ hours. The reaction mixture was poured into methyl acetate (300 cm$^3$), dried (anhydrous magnesium sulphate) and evaporated to oil. This oil was chromatographed on silica eluting with methyl acetate:toluene; 1:4. Fractions were collected containing the title compound Rf (SiO$_2$/methyl acetate:toluene; 1:4)=0.4 (detection by aqueous potassium permanganate spray), combined fractions were evaporated to afford an oil, yield=1.86 g (30%); ν (film) 1805, 1740, 1695, 745, 700 cm$^{-1}$, δ(CDCl$_3$) 2.28–2.82 (4H, m, NCH$_2$CH$_2$CO$_2$), 2.96 (1H, d, J 17 Hz, 6βCH), 3.05 (2H, d, J 7 Hz, 9CH$_2$), 3.41 (1H, dd, J 17 and 3 Hz, 6αCH), 3.45 (2H̄, s, NCH$_2$C$_6$H$_5$), 3.59 (3H, s, CO$_2$CH$_3$), 4.69 (1H, bt, J 7 Hz, 8CH̄), 5.04 (1H, bs, 3CH̄), 5.15 (2H, s, CO$_2$CH$_2$C$_6$H$_5$), 7.22 and 7.30 (2×5 H, 2×s, 2×CH$_2$C$_6$H$_5$).

(b) 9-N-(2'-Methoxycarbonylethyl)aminodeoxyclavulanic acid

Benzyl 9-N-(2'methoxycarbonylethyl)-N-benzylaminodeoxyclavulanate (1.7 g; 3.66 mmol) in ethanol (25 cm$^3$), tetrahydrofuran (15 cm$^3$) and water (5 cm$^3$) was hydrogenolysed at atmospheric pressure in the presence of 10% palladium on carbon (0.5 g; which had been prehydrogenated for 10 minutes) for 1.3 hours. The catalyst was filtered off and washed with ethanol (20 cm$^3$) then with aqueous ethanol (100 cm$^3$), this aqueous wash was evaporated to afford a white crystalline solid, the solid was washed with cold ethanol and dried to give 0.66 g of the title compound. The ethanolic catalyst washings were evaporated to an oil, ethanol was added and cooled, crystals formed slowly which after washing with ethanol and drying afforded a further 35 mg of the title compound; total yield=0.70 g (67%) Rf (SiO$_2$/ethyl acetate:ethanol:H$_2$O; 5:3:3)=0.45 (detection by aqueous potassium permanganate spray). (D$_2$O) CH$_3$CN 2.00 as internal standard; 2.78 (2H, t, J 6

Hz, CH$_2$CO$_2$), 3.08 (1H, d, J 17 Hz, 6βCH), 3.25 (2H, 6, NCH$_2$CH$_2$, J 6 Hz), 3.56 (1H, dd, J 17 and 3 Hz, 6αCH), 3.67 (3H, s, CO$_2$CH$_3$), 3.74 (2H, d, J 7.5 Hz, 9CH$_2$), 4.78 (1H, dt, J 7.5 and 1 Hz, 8CH), 4.97 (1H, bs, 3CH), 5.75 (1H, d, J 3 Hz, 5αCH). (KBr) 1805, 1740, 1700, 1610, 1575, 1430, 1404, 1378, 1315, 1305, 1223, 1205, 1192, 1125, 1075, 1043, 1025, 1005, 920, 896, 815, 792, 769 cm$^{-1}$.

EXAMPLE 7

(a) N,O-Dibenzyl β-alanine

β-Alanine benzyl ester (7.3 g; 45 mmol) was dissolved in chloroform (150 cm$^3$) and treated with benzaldehyde (1.2 equivalents) and stirred for 1½ hours. Benzyl alcohol (5 cm$^3$) was added followed by excess sodium borohydride. The reaction mixture was filtered and washed with saturated brine (3×200 cm$^3$), dried (anhydrous magnesium sulphate) and evaporated to an oil. This oil was dissolved in ether (300 cm$^3$) and treated with excess para-toluene sulphonic acid in ether. The resultant white solid was filtered off, washed with dry ether and dried to afford 12.83 g (65%) of N,O-dibenzyl β-alanine p-toluene sulphonate. This salt was stirred vigorously in ethyl acetate (150 cm$^3$) and water (150 cm$^3$) whilst being treated with sodium hydroxide solution to pH 10. The ethyl acetate phase was washed with saturated brine (5×200 cm$^3$), dried (anhydrous magnesium sulphate) and evaporated to afford 7.3 g (60%) of the title compound as an oil. (film) 3320, 1746, 1495, 1452, 1382, 1350, 1168, 740, 700 cm$^{-1}$. (CDCl$_3$) 1.81 (1H, s, exchanges with D$_2$O, NH), 2.4–3.1 (4H, m, NCH), 5.12 (2H, s, OCH$_2$C$_6$H$_5$), 7.29 and 7.34 (2×5H, 2×s, 2×CH$_2$C$_6$H$_5$), C$_{17}$H$_{18}$NO$_2$ (M$^+$—H) requires 268.1336; 268.1355; found, m/e 270 (M$^+$+H), 269 (M$^+$), 268 (M$^+$—H), 178 (M$^+$—91), 120, 118, 107, 106, 92, 91, 65.

(b) Benzyl 9-N-(2'-benzyloxycarbonylethyl)-N-benzylaminodeoxyclavulanate

Benzyl dichloroacetylclavulanate (5.24 g; 13.1 mmol) in dry dimethylformamide (50 cm$^3$) at −10° C. was treated with 1.9 equivalents of N,O-dibenzyl β alanine (6.7 g) in dimethylformamide (20 cm$^3$), dropwise over 10 minutes, then stirred for 1¼ hours between 0° and +10°. The reaction mixture was poured into ethyl acetate (250 cm$^3$) and washed with water (4×200 cm$^3$) and saturated brine (4×200 cm$^3$), dried (anhydrous magnesium sulphate) and evaporated to an oil. This oil was chromatographed on silica eluting with toluene-ethyl acetate; 4:1. Fractions were collected containing the title compound, Rf (SiO$_2$/toluene:ethyl acetate; 4:1)=0.6 (detection by aqueous potassium permanganate spray). Combined fractions were evaporated to afford the title compound as an oil 2.9 g (41%). (film) 1805, 1740, 1700, 740, 700 cm$^{-1}$, (CDCl$_3$) 2.36–2.90 (4H, brm, NCH$_2$CH$_2$CO$_2$), 2.93 (1H, d, J 17 Hz, 6βCH), 3.15 (2H, d, J 7 Hz, 9CH$_2$), 3.38 (1H, dd, J 17 and 3 Hz, 6αCH), 3.45 (2H, s, NCH$_2$C$_6$H$_5$), 4.68 (1H, bt, J 7 Hz, 8CH), 5.02 (1H, s, 3CH), 5.07, 5.15 (2H×2H, 2×s, 2×CO$_2$CH$_2$C$_6$H$_5$), 5.58 (1H, d, J 3 Hz, 5αCH), [7.22 (5H, s), 7.30 (10H, s), 3×CH$_2$C$_6$H$_5$].

(c) 9-N-(2'-Carboxyethyl)aminodeoxyclavulanic acid

Benzyl 9-N-(2'-benzyloxycarbonylethyl)-N-benzylaminodeoxyclavulanate 2.88 g; 5.33 mmol) in ethanol (30 cm$^3$), tetrahydrofuran (20 cm$^3$) and water (5 cm$^3$) was hydrogenolysed for 1 hour in the presence of 0.9 g of 10% palladium on carbon. The reaction mixture was filtered and the solids washed with ethanol (20 cm$^3$), then with aqueous ethanol (300 cm$^3$). The aqueous washings were evaporated to afford a white crystalline solid, this solid was slurried in cold methanol and filtered, washed with cold methanol and dried to afford 0.70 g (49%) of the title compound. The ethanolic catalyst washings were evaporated to an oil, redissolved in aqueous methanol (30 cm$^3$) (H$_2$O:MeOH; 1:6) and rehydrogenolysed with 100 mg of fresh palladium on carbon for 1½ hours. The solids were filtered off, washed with ethanol (20 cm$^3$) then with water (100 cm$^3$), the water washings were evaporated, methanol added (30 cm$^3$) and cooled, the resultant crystals were filtered off, washed with cold methanol and dried to afford a further 140 cm (9.7%) of the title compound. Total yield 0.84 g (58%), (Nujol) 1810, 1730, 1705, (1680–1505) cm$^{-1}$, the proton magnetic resonance spectrum was consistant with the desired compound.

EXAMPLE 8

(a) Methyl 9-N-(2-benzyloxycarbonylethyl)-N-benzylaminodeoxyclavulanate

Methyl dichloroacetylclavulanate (4.5 g; 13.9 mmol) in dry dimethylformamide (50 cm$^3$) at −10° was treated with 1.9 equivalents of N,O-dibenzyl β-alanine (7.1 g) and stirred for 2¾ hours between −10° and +20°. The mixture was poured into ethyl acetate (300 cm$^3$) and washed with water (5×100 cm$^3$) and saturated brine (5×100 cm$^3$), dried (anhydrous magnesium sulphate) and evaporated to an oil. This crude product was chromatographed on silica eluting with toluene:ethyl acetate; 4:1, fractions were collected containing the title compound Rf (SiO$_2$/toluene-ethyl acetate; 4:1)=0.5 (detection by aqueous potassium permanganate spray), combined fractions were evaporated to afford an oil, yield=0.97 (15%) (film) 1805, 1750, 1700, 1495, 1455, 1440, 1310, 1240, 1180, 1120, 1010, 740, 700 cm$^{-1}$. (CDCl$_3$) 2.36–2.95 (4H, m, NCH$_2$CH$_2$CO$_2$), 2.95 (1H, d, J 17 Hz, 6βCH), 3.17 (2H, d, J 7 Hz, 9CH$_2$), 3.40 (1H, dd, J 17 and 3 Hz, 6αCH), 3.53 (2H, s, NCH$_2$C$_6$H$_5$), 3.72 (3H, s, CO$_2$CH$_3$), 4.70 (1H, t, J 7 Hz, 8CH), 5.00 (1H, s, 3CH), 5.08 (2H, s, CO$_2$CH$_2$C$_6$H$_5$), 5.60 (1H, d, J 3 Hz, 5αCH), 7.23 and 7.23 (2×5H, 2×s, 2×CH$_2$C$_6$H$_5$).

(b) Methyl 9-N-(2'-carboxyethyl)aminodeoxyclavulanate

Methyl 9-N-(2'-benzyloxycarbonylethyl)-N-benzylaminodeoxyclavulanate (0.87 g; 1.88 mmol) in ethanol (15 cm$^3$), tetrahydrofuran (10 cm$^3$) and water (5 cm$^3$) was hydrogenolysed at atmospheric pressure in the presence of 10% palladium on carbon (260 mg; which had been prehydrogenated for 15 minutes), for 4¼ hours. The catalyst was filtered off and the filtrate evaporated to a foam, yield=1.1 g. 0.6 g of this crude product was chromatographed on silica eluting with ethyl acetate-ethanol-water (5:4:3), fractions were collected containing the title compound Rf (SiO$_2$/ethyl acetate-ethanol-water; 5:2:2)=0.33 (detection by aqueous potassium permanganate spray). Combined fractions were evaporated to afford 200 mg of a foam. (KBr) 1800, 1745, 1700, 1625 (shoulder), 1590 cm$^{-1}$.

EXAMPLE 9

(a) Benzyl 9-N-(5'-benzyloxycarbonylpentyl)-N-benzylaminodeoxyclavulanate

Benzyl dichloroacetylclavulanate (8.12 g; 20.3 mmol) in dry dimethylformamide (70 cm$^3$) at −15° was treated with 1.9 equivalents of N-benzyl(5'-benzyloxycarbonylpentyl)amine dropwise in dimethylformamide and stirred for 35 minutes between −15° and −10°. The mixture was poured into ethyl acetate (300 cm$^3$) and was washed with water (4×100 cm$^3$) and saturated brine (6×100 cm$^3$) dried and evaporated in the presence of toluene to low volume. This crude product was chromatographed on silica eluting with toluene-ethyl acetate (4:1). Fractions were collected containing the title compound Rf (SiO$_2$/toluene-ethyl acetate; 4:1)=0.5 (detection by aqueous potassium permanganate spray), combined fractions were evaporated to an oil, yield=1.5 g (13%), (film) 1805, 1740, 1700, 1498, 1455, 1305, 1172, 1015, 740, 700 cm$^{-1}$.

(b) 9-N-(5'-Carboxypentyl)aminodeoxyclavulanic acid

Benzyl 9-N-(5'-benzyloxycarbonylpentyl)-N-benzylaminodeoxyclavulanate (1.43 g; 2.45 mmol) in ethanol (20 cm$^3$), tetrahydrofuran (10 cm$^3$) and water (4 cm$^3$) was hydrogenolysed in the presence of 10% palladium on carbon (400 mg which had been prehydrogenated for 10 minutes) for 21 hours at atmospheric pressure. The catalyst was filtered off and washed with ethanol (20 cm$^3$) then with aqueous ethanol (100 cm$^3$), this aqueous washing was evaporated to afford a white crystalline solid which was washed with ice cold ethanol and dried to give 265 mg of the title compound, Rf (SiO$_2$/ethyl acetate-ethanol-water; 5:3:3)=0.55 (detection by aqueous potassium permanganate spray). The initial filtrate and ethanolic washings were evaporated to afford an oil. This oil was rehydrogenolysed in aqueous ethanol with 200 mg palladium on carbon for 4½ hours to afford a further 65 mg of the title compound; total yield=330 mg (44%). (Nujol) 1805, 1705, 1695 (shoulder), 1615, 1580, 1300, 1190, 1050, 1020, 1008, 895, 758 cm$^{-1}$, 'KBr' 1800, 1708, 1620, 1590, 1300, 1203, 1190, 1125, 1050, 1020, 895 cm$^{-1}$. (D$_2$O/DMSO D6, 1.15–1.90 (6H, bm, NCH$_2$(CH$_2$)$_3$CH$_2$), 2.15–247 (2H, m, CH$_2$CO$_2$H), 2.80–3.10 (2H, m, N$^\oplus$CH$_2$(CH$_2$)$_3$), 3.07 (1H, d, J 17 Hz, 6βCH), partially obscured), 3.58 (1H, dd, J 17 and 2.5 Hz, 6αCH, partially obscured), 3.67 (2H, d, J 8 Hz, 9CH$_2$), 8CH obscured by HOD at 4.60, 4.91 (1H, s, 3CH), 5.74 (1H, d, J 2.5 Hz, 5αCH).

EXAMPLE 10

(a) Benzyl 9-N-(3'-benzyloxycarbonylpropyl)-N-benzylaminodeoxyclavulanate

Benzyl dichloroacetylclavulanate (14.35 g; 36 mmol) in dry dimethylformamide (100 cm$^3$) at −10° was treated with 1.9 equivalents of N,O-dibenzyl-4-aminobutyric acid (19.4 g dropwise in dimethylformamide over 10 minutes. Stirring was continued for 1¼ hours between −10° and 0° C. The reaction mixture was poured into ethyl acetate (500 cm$^3$) and washed with water (4×100 cm$^3$), saturated brine (6×150 cm$^3$), dried (anhydrous magnesium sulphate) and evaporated in the presence of toluene to low volume. This crude product was chromatographed on silica eluting with toluene-ethyl acetate (4:1). Fractions were collected containing the title compound Rf (SiO$_2$/toluene-ethyl acetate; 4:1)=0.4 (detection by aqueous potassium permanganate spray). Combined fractions were evaporated to afford 5.6 g (28%) of an oil. (film) 1805, 1740, 1700, 1500, 1455, 1307, 1172, 1015, 740, 700 cm$^{-1}$, (CDCl$_3$) 1.60–1.94 (2H, m, NCH$_2$CH$_2$CO$_2$), 2.15–2.50 (4H, m, NCH$_2$CH$_2$CH$_2$CO$_2$), 2.91 (1H, d, J 17 Hz, 6βCH), 3.12 (2H, d, J 7 Hz, 9CH$_2$), 3.35 (1H, dd, J 17 and 3 Hz, 6αCH), 3.41 (2H, s, NCH$_2$C$_6$H$_5$), 4.68 (1H, bt, J 7 Hz, 8—CH), 5.03 (1H, s, 3CH), [5.05 (2H, s) and 5.14 (2H, s) 2×CO$_2$CH$_2$C$_6$H$_5$], 5.57 (1H, d, J 3 Hz, 5αCH), [7.21 (5H, s) and 7.30 (10H, bs), 2×OCH$_2$C$_6$H$_5$].

(b) 9-N-(3'-Carboxypropyl)aminodeoxyclavulanic acid

Benzyl 9-N-(3'-benzyloxycarbonylpropyl)-N-benzylaminodeoxyclavulanate (2 g; 3.6 mmol) in ethanol (30 cm$^3$) tetrahydrofuran (15 cm$^3$) and water (5 cm$^3$) was hydrogenolysed in the presence of 10% palladium on carbon (0.6 g; which had been prehydrogenated for 10 minutes) for 2½ hours at atmospheric pressure. The catalyst was filtered off and washed with ethanol (30 cm$^3$) then with water (50 cm$^3$), this aqueous washing was collected separately and was evaporated in the presence of ethanol to a white crystalline solid. The solid was washed with cold ethanol and dried to afford 365 mg of the title compound. The initial filtrate and ethanolic washings were rehydrogenated with the original catalyst for a further 16 hours. The catalyst was filtered off and washed with aqueous ethanol (20 cm$^3$). The filtrate was evaporated to an oil, to which methanol was added and cooled (0°), crystals formed which were filtered off, washed with cold methanol and dried to afford a further 103 mg of the required product. Total yield=0.47 g (46%), Rf (SiO$_2$/ethyl acetate-ethanol-water; 5:3:3)=0.33 (detection by aqueous potassium permanganate spray), (Nujol) 1802, 1900, 1595, 1575, 1300, 1187, 1122, 1045, 1020, 1005, 915, 895, 852, 790, 760 cm$^{-1}$, (D$_2$O) CH$_3$CN internal standard at 1.98; 1.70–2.10 (2H, m, NCH$_2$CH$_2$CH$_2$CO$_2$H), 2.31 (2H, t, J 7 Hz, CH$_2$CO$_2$H), 3.00 (2H, t, J 7 Hz, N$^\oplus$H$_2$CH$_2$CH$_2$), 3.07 (1H, d, J 17 Hz, 6βCH), 3.55 (1H, dd, J 17 and 3 Hz, 6αCH), 3.70 (2H, d, J 7 Hz, 9 CH$_2$), 4.78 (1H, bt, J 7 Hz, 8CH), 4.99 (1H, s, 3CH), 5.73 (1H, d, J 3 Hz, 5αCH).

EXAMPLE 11

(a) Benzyl 9-N-(10'-benzyloxycarbonyldecyl)-N-benzylaminodeoxyclavulanate

Benzyldichloroacetylclavulanate (9.7 g; 24.2 mmol) in dry dimethylformamide (80 cm$^3$) at −10° was treated with 1.9 equivalents of N,O-dibenzyl 11-aminoundecanoic acid (in 20 cm$^3$ dimethylformamide) dropwise over 10 minutes and then at −10° to −5° over 40 minutes with vigorous stirring. The mixture was poured into ethylacetate (350 cm$^3$) washed with water (5×150 cm$^3$) and saturated brine (5×150 cm$^3$), dried (anhydrous magnesium sulphate) and evaporated to an oil. This crude product was chromatographed on silica eluting with ethylacetate-toluene (:4), fractions were collected containing the title compound, Rf (SiO$_2$/ethyl-acetate-toluene; 1:4)=0.5 (detection by aqueous potassium permanganate spray). Combined fractions were evaporated to afford the title compound as an oil, yield=6.24 g (40%) ν (film) 1805, 1737, 1700 (shoulder), 1305, 1170, 1005, 740, 700 cm$^{-1}$, δ(CDCl$_3$) 1.0–1.80 (16H, broad m, NCH$_2$(CH$_2$)$_8$CH$_2$CO$_2$), 2.33

(4H, broad t, J 7 Hz, NCH$_2$(CH$_2$)$_8$CH$_2$CO$_2$), 2.93 (1H, d, J 17 Hz, 6$\beta$CH), 3.15 (2H, d, J 7 Hz, 9CH$_2$), 3.40 (1H, dd, J 17 and 3 Hz, 6$\alpha$CH), 3.43 (2H, s, NCH$_2$C$_6$H$_5$), 4.72 (1H, t, J 7 Hz, 8CH), 5.05 (1H, s, 3CH), [5.08 (2H, s), 5.16 (2H, s) 2×OCH$_2$C$_6$H$_5$], 5.60 (1H, d, J 3 Hz, 5$\alpha$CH), [7.24 (5H, s), 7.32 (10H, broad s), 2×OCH$_2$C$_6$H$_5$, NCH$_2$C$_6$H$_5$].

(b) 9-N-(10'-Carboxydecyl)aminodeoxyclavulanic acid

Benzyl 9-N-(10'-benzyloxycarbonyldecyl)-N-benzylaminodeoxyclavulanate (3 g; 4.6 mmol) in ethanol (25 cm$^3$), tetrahydrofuran (25 cm$^3$) and water (5 cm$^3$) was hydrogenolysed at atmospheric pressure in the presence of 1 g 10% palladium on carbon for 2½ hours. The catalyst was filtered off and washed with ethanol; then with aqueous ethanol (150 cm$^3$), this aqueous washing was collected separately and evaporated to a white crystalline solid; this solid was washed with tetrahydrofuran-ethanol and dried to afford 430 mg (24%) of the title compound. The ehtanolic washings and initial filtrate was rehydrogenated with the original catalyst for 30 minutes. The catalyst was filtered off and washed with aqueous ethanol, the filtrate was evaporated to an oil, tetrahydrofuran (10 cm$^3$) was added and the solution cooled, crystals formed which were filtered off cold and washed with tetrahydrofuran (0°), drying afforded a further 0.32 g (18%) of the title compound; total yield=0.75 g (42%) Rf (SiO$_2$/ethylacetate-ethanol-water; 5:3:3)=0.70 (detection by aqueous potassium permanganate spray), $\nu$ (Nujol) 1807, 1720, 1695, 1600 (broad), 1298, 1182, 1060, 895, 750 cm$^{-1}$, $\nu$(KBr) 1808, 1720, 1695, 1600, 1397, 1295, 1183, 1130, 1057, 1022, 892, 750 cm$^{-1}$, $\delta$(D$_2$O/C$_5$D$_5$N; 2:1) 0.75–1.90 (16H, broad m, NCH$_2$(CH$_2$)$_8$CH$_2$), 2.23 (2H, t, J 7 Hz, NCH$_2$(CH$_2$)$_9$CH$_2$CO$_2$H), 2.99 (2H, t, J 7 Hz, NCH$_2$(CH$_2$)$_8$CH$_2$), 3.02 (1H, d, J 17 Hz, 6$\beta$CH), 3.59 (1H, dd, J 17 and 3 Hz, 6$\alpha$CH), 3.75 (2H, d, J 7 Hz, 9CH$_2$), 8CH obscured by HOD at 4.95, 5.06 (1H, s, 3CH), 5.85 (1H, d, J 3 Hz, 5$\alpha$CH); internal standard CH$_3$CN at $\delta$ 2.00.

EXAMPLE 12

(a) O-Benzyl trans-4-(Aminomethyl)cyclohexane carboxylic acid

Trans-4-Aminomethyl cyclohexane carboxylic acid (25 g; 160 mmol) in benzyl alcohol (100 cm$^3$) and toluene (50 cm$^3$) with para-toluene sulphonic acid monohydrate (30.2 g; 1 equivalent) was refluxed for 17½ hours using a Dean and Stark apparatus to collect the water of condensation and from the toluene sulphonic acid monohydrate. The clear reaction mixture was poured into ether (600 cm$^3$) and the resultant white solid filtered off, washed with ether and dried to afford 57 g (85%) of the title compound. Both infrared and nuclear magnetic resonance spectra were consistant with the desired compound.

(b) N,O-Dibenzyl-trans-4-aminomethylcyclohexanecarboxylic acid

O-Benzyl-4-trans aminomethyl-cyclohexanecarboxylic acid para-toluene sulphonate (30 g; 72 mmol) in CHCl$_3$ (150 cm$^3$) was treated with triethylamine (10.5 cm$^3$; 1 equivalent), then with benzaldehyde (1 equivalent), benzylalcohol (20 cm$^3$) and stirred for 1 hour. To the reaction mixture was added excess sodium borohydride in small portions, the excess was destroyed by adding water until effervescence ceased. The reaction mixture was diluted with chloroform (150 cm$^3$) and washed with saturated brine (5×150 cm$^3$), dried (anhydrous magnesium sulphate) and evaporated to an oil. This oil was dissolved in diethyl ether (600 cm$^3$) and treated with excess para-toluene sulphonic acid in ether. The resultant white para-toluene sulphonate salt was filtered off, washed with ether and dried to afford 27 g of a white crystalline solid. This solid was stirred vigorously in ethyl acetate-water whilst being treated with aqueous sodium hydroxide to pH 10. The ethyl acetate phase was washed with brine (5×150 cm$^3$) dried and evaporated to an oil which crystallised to an off white solid, yield=17 g (70%) (DBr) 3305, 1720, 1450, 1256, 1185, 1125, 1010, 805, 747, 733, 695 cm$^{-1}$, $\delta$(CDCl$_3$) 0.6–2.6 (10H, m, C$_6$H$_{10}$), 2.00 (1H, s, exchanges with D$_2$O, NH), 2.45 (2H, d, J 5 Hz, NCH$_2$CH), 3.75 (2H, s, NCH$_2$C$_6$H$_5$), 5.09 (2H, s, OCH$_2$C$_6$H$_5$), 7.31 (10H, bs, 2×CH$_2$C$_6$H$_5$). C$_{22}$H$_{27}$NO$_2$ requires 337.2040, 337.2035 found, m/e 337 (M+), 120 (100% I), 106, 91, 65.

(c) Benzyl 9-N-(4'-trans-benzyloxycarbonylcyclohexylmethyl)-N-benzylaminodeoxyclavulanate Benzyldichloroacetylclavulanate (10.4 g; 26 mmol) in dry dimethylformamide (80 cm$^3$) at −10° was treated with 1.9 equivalents of N,O-dibenzyl 4-trans aminomethylcyclohexanecarboxylic acid (16.6 g) in dimethylformamide (50 cm$^3$), dropwise over 10 minutes, then stirred for 3 hours between −10° and +10°. The mixture was poured into ethyl acetate (300 cm$^3$), dried (anhydrous magnesium sulphate) and evaporated to low volume in the presence of toluene. This crude product was chromatographed on silica eluting with toluene-ethylacetate (5:1), fractions were collected containing the title compound and combined fractions were evaporated to afford the title compound as an oil; 3.94 g (25%), $\nu$(film) 1805, 1735, 1700 (shoulder), 1455, 1305, 1175, 1010, 745, 700 cm$^{-1}$. The proton magnetic resonance spectra was consistent with the desired product.

(d) 9-N-(trans-4'-Carboxycyclohexylmethyl)aminodeoxyclavulanic acid

Benzyl 9-N-(trans-4'-benzyloxycarbonylcyclohexylmethyl)-N-benzylamino deoxyclavulanate (3.6 g; 5.9 mmol) in tetrahydrofuran (50 cm$^3$) and water (5 cm$^3$) was hydrogenolysed for 33 minutes at atmospheric pressure in the presence of 10% palladium on charcoal (1.2 g; which had been prehydrogenated for 10 minutes), the catalyst was filtered off and washed with tetrahydrofuran (50 cm$^3$), then separately with 200 cm$^3$ of a mixture of ethanol-tetrahydrofuran and water (1:1:2). This aqueous washing was collected and evaporated to afford 1.0 g (50%) of the title compound as a white crystalline solid from cold ethanol. The initial reaction filtrate and tetrahydrofuran washings were evaporated to an oil, ethanol was added and on cooling crystals formed with when filtered off and washed with cold ethanol afforded (after drying) a further 70 mg of the desired product. Rf (SiO$_2$/ethylacetate:ethanol:water; 5:3:3)=0.4 (detection by aqueous potassium permanganate spray), $\nu$(Nujol) 1798, 1695, 1610, 1580, 1305, 1187, 1127, 1055, 1020, 935, 100 cm$^{-1}$, $\nu$(DBr) 1795, 1700, 1600 (broad), 1452, 1400, 1302, 1185, 1125, 1020, 935, 895 cm$^{-1}$. $\delta$(D$_2$O/pyridine d-5) 0.5–2.0 (10H, broad m, CH$_2$C$_6$H$_{10}$CO$_2$H), 2.49 (2H, d, J 6 Hz, N$^\oplus$CH$_2$C$_6$H$_{10}$), 2.70 (1H, d, J 17 Hz, 6$\beta$CH), 3.23 (1H, dd, J 17 and 3 Hz, 6αC$\underline{H}$), 3.37 (2H, d, J 8 Hz, 9C$\underline{H}_2$), 8CH obscured by HOD at δ4.50, 4.67 (1H, s, 3C$\underline{H}$), 5.46 (1H, d, J 3 Hz, 5αC$\underline{H}$).

EXAMPLE 13

(a) Benzyloxycarbonylmethyl 9-(N-benzyl-N-benzyloxycarbonylmethyl)amino-9-deoxyclavulanate A stirred suspension of 9-amino-9-deoxyclavulanic acid (400 mg, 2.0 mmol) in dry DMF (20 ml) was cooled to 0° and treated with DBN (750 mg, 6.0 mmol). After 2 minutes the solution was treated with benzyl bromide (0.24 ml, 2.0 mmol) and stirred at 0° for 35 minutes before the addition of benzyl bromoacetate (1 ml). Stirring was continued for a further 2½ hours at room temperature.

The reaction mixture was diluted with ethyl acetate and washed well with water. The ethyl acetate layer was dried (MgSO$_4$) and evaporated to afford an oil which was chromatographed on silica gel. Elution with EtOAc/cyclohexane (1:2) gave the desired product as an oil (109 mg, 9%).

$\nu_{max}$ (liq. film) 1800, 1750, 1700, 1160 cm$^{-1}$.

δ(CDCl$_3$) 2.87 (1H, d, J 17 Hz, β-lactam CH$\underline{H}$), 3.30 (1H, dd, J 17 and 3 Hz β-lactam CH$\underline{H}$), 3.30 (2h, s, NC$\underline{H}_2$Ph), 3.35 (2H, d, J 7 Hz, C(9)$\underline{H}$), 3.72 (2H, s, NC$\underline{H}_2$CO$_2$), 4.62 (2H, s, OC$\underline{H}_2$CO$_2$), 4.81 (1H, t, J 7 Hz, vinyl $\underline{H}$), 5.09 (5H, s, OC$\underline{H}_2$Ph and C(3)$\underline{H}$), 5.50 (1H, d, J 3 Hz, β-lactam C$\underline{H}$), 7.29 (15H, s, aryl $\underline{H}$) ppm.

Continued elution with the same solvent afforded the ester of an oil (168 mg, 13%). This material has been prepared previously.

(b) Lithium 9-(N-benzyl-N-benzyloxycarbonylmethyl)amino-9-deoxyclavulante

A solution of the ester (i) above (100 mg) in aqueous tetrahydrofuran was stirred at room temperature and treated with 1M LiOH solution dispensed from an automatic burette at such a rate as to keep the pH of the solution to 10±0.5. The reaction was terminated when 1 equivalent of LiOH had been consumed (3 hours). Dilute hydrochloric acid was then added dropwise to bring the pH to 7.0.

The resulting solution was evaporated to dryness and triturated with ether to afforded the desired salt as a white solid (62 mg, 80%).

$\nu_{max}$ (Nujol) 1790, 1730, 1710, 1610 cm$^{-1}$.

δ (D$_2$O) 2.65 (1H, d, J 17 Hz, β-lactam CH$\underline{H}$), 3.10 (2H, s, NC$\underline{H}_2$Ph), ca 3.2 (3H, overlapping signals, β-lactam CH$\underline{H}$ and C(9)H), 3.52 (2H, s, NC$\underline{H}_2$CO$_2$), 4.80 (1H, s, C(3)H), 4.87 (2H, s, OC$\underline{H}_2$Ph), 5.54 (1H, broad s, β-lactam C$\underline{H}$), 7.13 and 7.18 (10H, aryl $\underline{H}$) ppm.

(c) Lithium 9-N-(carboxymethyl)amino-9-deoxyclavulanate

A solution of lithium 9-(N-benzyl-N-benzyloxycarbonylmethyl)amino-9-deoxyclavulanate (32 mg) in water (20 ml), containing THF (5 ml), was hydrogenated over 10% Pd/$^C$ (20 mg) for 4 hours at ambient temperature and pressure. The catalyst was filtered off and the solution evaporated to afford the desired product as a white solid (18 mg, 95%).

$\nu_{max}$ (KBr) 1780, 1720, 1620 cm$^{-1}$.

δ(D$_2$O) 3.10 (1H, d, J 17 Hz, β-lactam CH$\underline{H}$), 3.56 (1H, dd, J 17 and 3 Hz, β-lactam CH$\underline{H}$), 3.50 (2H, s, NC$\underline{H}_2$CO$_2$H), 3.72 (2H, d, J 7 Hz, C(9)$\underline{H}$), 4.79 (1H, t, J 7 Hz, vinyl $\underline{H}$), 4.99 (1H, s, C(3)$\underline{H}$), 5.73 (1H, d, J 3 Hz, β-lactam C$\underline{H}$) ppm.

EXAMPLE 14

(a) Nα-Benzyloxycarbonyl-O-benzyl-(L)-lysine-p-toluene sulphonate

Nα-Banzyloxycarbonyl (L) lysine (10 g; 35.7 mmol) in benzyl alcohol (30 cm$^3$), toluene (30 cm$^3$) and para toluene sulphonic acid (6.93 g) was heated under reflux. The water evolved from the reaction and from the p-toluene sulphonic acid monohydrate was collected azeotropically using a Dean and Stark apparatus. Refluxing was continued until the water was no longer collected. The reaction mixture was allowed to cool, when crystals formed. The crystals were filtered off and dried, yield=5 g. The proton magnetic resonance and infrared spectra showed this compound to be the p-toluene sulphonic acid salt of the starting material. The filtrate was poured into ether (300 cm$^3$) forming an oil. The ether was decanted off and the oil washed with ether and dried under reduced pressure. The resultant oil slowly crystallised to afford 12 g (62%) of the title compound, ν (Nujol) 3370, 1735, 1692, 1040, 1015, 820, 745, 735, 700, 685 cm$^{-1}$.

The 5 g of recovered Nα-benzyloxycarbonyl paratoluene sulphonate was re-enacted with benzyl alcohol (20 cm$^3$), toluene (20 cm$^3$) and 0.1 equivalent of para-toluene sulphonic acid under reflux using a Dean and Stark for 20 hours. The reaction mixture was cooled, then poured into ether, forming an oil, which crystallised slowly to afford a further 5.5 g of the title compound. Total yield=17.5 g (90.4%).

(b) Nε,O-dibenzyl-Nα-benzyloxycarbonyl(L) lysine

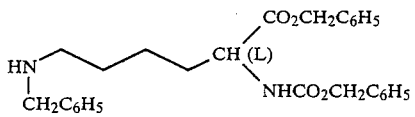

Nα-Benzyloxycarbonyl-O-benzyl(L) lysine paratoluene sulphonate (5.5 g) in water (100 cm$^3$) and ethyl acetate (200 cm$^3$) was treated with sodium carbonate to pH 10. The ethyl acetate phase was washed with saturated brine (3×200 cm$^3$), dried (anhydrous magnesium sulphate) and evaporated to an oil, yield=4.4 g of free amino compound. This was dissolved in chloroform (100 cm$^3$), benzyl alcohol (10 cm$^3$) and treated with 1.2 equivalents of benzaldehyde, stirred for 2 hours then treated with excess sodium borohydride. The solids were filtered off and the filtrate washed with saturated brine (5×150 cm$^3$), dried and evaporated to an oil. This oil was dissolved in ether (300 cm$^3$) and treated with para-toluene sulphonic acid in ether until in slight excess. An oil formed which crystallised at −10° overnight. The crystals were filtered off and washed with dry ether, then treated with sodium carbonate whilst stirring vigorously in ethyl acetate and water to pH 10. The organic phase was washed with saturated brine (4×100 cm$^3$), dried and evaporated to afford the title compound as an oil, yield=3.1 g (57%) ν(film) 3330 (br), 1720, 750, 740, 700 cm$^{-1}$, δ(CDCl$_3$) 1.1–1.9 (6H, bm, NCH$_2$(C$\underline{H}_2$)$_3$CH), 1.20 (1H, s, exchanges+D$_2$O; CH$_2$N$\underline{H}$), 2.52 (2H, bt, J 6 Hz, NC$\underline{H}_2$(CH$_2$)$_3$), 3.69 (2H, s, NC$\underline{H}_2$C$_6$H$_5$), 4.20–4.52 (1H, bm,

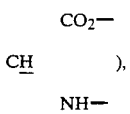

5.05 and 5.11 (2×2H, 2×s, 2×CO$_2$CH$_2$C$_6$H$_5$), 5.20–5.50 (1H, m, exchanges+D$_2$O; NHCO$_2$), 7.25 (5H, s) and 7.28 (10H, s); 3×CH$_2$C$_6$H$_5$. C$_{28}$H$_{32}$N$_2$O$_4$ requires 460.2359; 460.2367 found m/e 460 (M+), 369 (M+—91), 308, 262, 261, 174, 160, 155, 120, 106, 92, 91 (100% I), 65. The title compound was obtained as a white crystalline solid from ethyl acetate-cyclohexane, ν (NUJOL) 3320 (broad), 1725, 1687, 1535, 750, 725, 695 cm$^{-1}$. [α]$_D^{20}$ c=1% in chloroform=+0.61°.

(c) Benzyl 9-[Nε,(Nε,O-dibenzyl-Nα-Z-(L)lysyl)]deoxyclavulanate

Benzyl dichloroacetylclavulanate (2.36 g; 5.9 mmol) in dry dimethylformamide (30 cm$^3$) at −10° was treated with 1.9 equivalents of Nε, O-dibenzyl-Nα-Z-(L) lysine, dropwise in dimethylformamide (40 cm$^3$) over 10 minutes. Then stirred between −10° and +10° over 1¾ hours. The reaction mixture was poured into ethylacetate (200 cm$^3$) and washed with water (5×100 cm$^3$), saturated brine (3×100 cm$^3$) dried (anhydrous) magnesium sulphate) and evaporated to an oil. This oil was chromatographed on silica eluting with toluene—ethyl acetate (3:1), fractions were collected containing the title compound Rf (SiO$_2$/toluene:ethyl acetate; 2:1)=0.45 (detection by aqueous potassium permanganate spray). Combined fractions were evaporated to afford an oil, 1.63 g (38%), ν (film) 3370 (br), 1800, 1745, 1722, 1515, 1495, 1305, 1180, 1040, 1025, 1012, 740, 700 cm$^{-1}$, δ(CDCl$_3$) 1.0–2.4 (8H, bm, N(CH$_2$)$_4$CH), 2.90 (1H, d, J 17 Hz, 6βCH), 3.10 (2H, d, J 7 Hz, 9CH$_2$), 3.35 (1H, dd, J 17 and 3 Hz, 6αCH), 3.38 (2H, s, NCH$_2$C$_6$H$_5$), 4.17–4.50 (1H, bm, CH$_2$CH(NHCO$_2$CH$_2$C$_6$H$_5$)), 4.68 (1H, t, J 7 Hz, 8CH), 5.02 (1H, s, 3CH), [5.07 (2H, s); 5.13 (4H, s), 2×CO$_2$CH$_2$C$_6$H$_5$ and NCO$_2$CH$_2$C$_6$H$_5$], 5.20–5.40 (1H, bm, NH, partially obscured), 5.58 (1H, d, J 3 Hz, 5αCH), [7.21 (5H, s); 7.29 (15H, s), 3×CO$_2$CH$_2$C$_6$H$_5$ and NCH$_2$C$_6$H$_5$], [α]$_D^{20}$ (c=1.2% in chloroform)=+5.4°.

(d) 9-[Nε(L)-Lysyl)]deoxyclavulanic acid

Benzyl 9-[Nε(Nε,O-dibenzyl-N-Z-(L)lysyl)]deoxyclavulanate (1.38 g; 1.89 mmol) in ethanol (10 cm$^3$), tetrahydrofuran (15 cm$^3$) and water (3 cm$^3$) was hdyrogenolysed in the presence of 10% palladised carbon (450 mg; which had been prehydrogenolysed for 15 minutes) for 4½ hours. The catalyst was filtered off and washed with aqueous ethanol (100 cm$^3$). The filtrate was evaporated to an oil which was redissolved in aqeuous ethanol (50 cm$^3$) and rehydrogenolysed with 200 mg of fresh palladised carbon for 4 hours when thin layer chromatography showed the reaction to be complete. The catalyst was filtered off and washed with water. The filtrate was evaporated to afford an oil, which on trituration with propan-2-ol afforded the title compound as a cream coloured solid, yield=366 mg (59%) Rf (Sio$_2$/ethyl-acetate—ethanol—water; 1:1:1)=0.33 (detection by aqueous potassium permanganate spray) ν (KBr) 1790, 1690, 1620 (very broad), 1400, 1310, 1192, 1120, 1044, 1017 cm$^{-1}$. The proton magnetic resonance spectrum was consistent with the desired product.

EXAMPLE 15

2'-Phenyl methoxycarbonylmethyl-9-[N-(2'-phenylmethoxycarbonylmethyl)amino]-9-deoxyclavulanate (a) Methyl α-iodophenylacetate Sodium iodide (7.5 g, 0.05 mol) dissolved in analar acetone (25 ml) was stirred at room temperature and to it added methyl α-chlorophenylacetate (9.32 g, 0.05 mol). Stirred for 15 minutes. The precipitate sodium chloride was allowed to settle.

(b) 2'-Phenyl methoxycarbonylmethyl-9-[N-(2'-phenylmethoxycarbonylmethyl)amino]-9-deoxyclavulanate A suspension of 9-ADCA (198 mg, 1.0 mmol) in dry DMF (10 ml) was stirred at 0° and treated with DBN (375 mg, 3.0 mmol). After 2 minutes a solution of methyl α-iodophenylacetate in acetone (5 ml of above solution) was added in one portion and stirring at 0° maintained for 30 minutes. The solution was then allowed to warm to room temperature and stirring continued for a further 2½ hours.

The reaction mixture was diluted with ethyl acetate (ca 50 ml) and filtered. The filtrate was evaporated to an oil which was again triturated with ethyl acetate, filtered, and the solvent removed under reduced pressure. The resulting oil was chromatographed on silica gel eluting with ethyl acetate/cyclohexane (1:2) to afford the desired product as a yellow oil (22 mg, 5%).

ν$_{max}$ (liquid film) 1800, 1740, 1690, 1220, 1170 cm$^{-1}$.

δ (CDCl$_3$) 1.90 (1H, broad s, NH), 3.02 (1H, d, J 17 Hz, β-lactam CHH), 3.32 (2H, d, J 7 Hz, C(9)H), 3.43 (1H, dd, J 17 and 3 Hz, β-lactam CHH), 3.65 and 3.70 (6H, s, OCH$_3$), 4.31 and 4.42 (1H, s, NHCH), 4.95 (1H, t, J 7 Hz, vinyl H), 5.13 (1H, complex, C(3)H), 5.64 (1H, d, J 7 Hz, β-lactam CH), 5.93 and 5.99 (1H, s, —CO$_2$CH), 7.30 and 7.39 (10H, s, Aryl H) ppm.

EXAMPLE 16

Di(ethoxycarbonyl)methyl 9-N-[di(ethoxycarbonyl)methyl]-amino-9-deoxyclavulanate A suspension of 9-ADCA (198 mg, 1.0 mmol) in dry DMF (10 ml) was stirred at 0° and treated with DBN (250 mg, 2.0 mmol) in DMF (2 ml). After 2 minutes diethyl bromomalonate (10 ml) was added and stirring at 0° maintained for 30 minutes. The reaction mixture was allowed to warm to room temperature and stirring was continued for a further 2½ hours.

The DMF was removed under reduced pressure and the residue dissolved in ethyl acetate. After washing with a little water and ethyl acetate was evaporated and the resultant oil chromatographed on silica gel eluting with ethyl acetate/cyclohexane (1:3→1:1). The desired product was obtained as an oil (11 mg, 2%).

ν$_{max}$ (CHCl$_3$) 3300, 1805, 1750, 1740, 1690 cm$^{-1}$.

δ (CDCl$_3$) 1.23 (6H, t, J 7 Hz, CH$_2$CH$_3$), 1.27 (6H, t, J 7 Hz, CH$_2$CH$_3$), 3.02 (1H, d, J 17 Hz, β-lactam CHH), 3.34 (2H, d, J 7 Hz, C(9)H), 3.45 (1H, dd, J 17 and 3 Hz, β-lactam CHH), 4.00 (1H, s, NHCH), 4.10–4.37 (8H, complex, OCH$_2$CH$_3$), 4.85 (1H, t, J 7 Hz, vinyl H), 5.15 (1H, s, C(3)H), 5.50 (1H, s, OCH), 5.66 (1H, d, J 3 Hz, β-lactam CH) ppm.

PHARMACOLOGY

Synergistic Activity with Amoxycillin

Using conventional methods the following results were obtained in a standard MIC test:

| Amoxycillin and Compound of Example No | | MIC μg/ml amoxycillin | | |
|---|---|---|---|---|
| | | St aureus Russell | K aerogenes E70 | E coli JT39 |
| 1(b) | 5.0 μg/ml | 0.08 | 2.0 | 1.0 |
| | 1.0 μg/ml | 0.3 | 6.0 | 4.0 |
| 3(c) | 5.0 μg/ml | 0.08 | 3.1 | 4.0 |
| | 1.0 μg/ml | 0.6 | 12.5 | 8.0 |
| 4(c) | 5.0 μg/ml | — | 6.2 | 4.0 |
| | 1.0 μg/ml | 0.15 | 25 | 31.2 |
| 6(b) | 5.0 μg/ml | — | 3.1 | 4.0 |
| | 1.0 μg/ml | 0.15 | 6.2 | 8.0 |
| 9(b) | 5.0 μg/ml | 0.08 | 3.1 | 4.0 |
| | 1.0 μg/ml | 1.25 | 12.5 | 16 |
| 10(b) | 5.0 μg/ml | 1.25 | 3.1 | 4.0 |
| | 1.0 μg/ml | 2.5 | 12.5 | 31.2 |
| 11(b) | 20 μg/ml | — | 12.5 | 8.0 |
| | 5.0 μg/ml | — | 12.5 | 31.2 |
| 12(d) | 5.0 μg/ml | 0.15 | 1.5 | 4.0 |
| | 1.0 μg/ml | 1.25 | 12.5 | 31.2 |
| 14(d) | 5.0 μg/ml | 0.15 | 3.1 | 4.0 |
| | 1.0 μg/ml | 0.6 | 6.2 | 16 |
| Amoxycillin alone | | 500 | 500 | 2000 |

The amines had no activity alone at the above concentrations.

Antibacterial Activity

Using conventional methods the following results were obtained in a standard MIC test:

| Compound of Example No | St aureus Russell | K aerogenes E70 | E coli JT39 |
|---|---|---|---|
| 1(b) | 31.0 | >500 | 15 |
| 3(c) | 31.0 | 250 | 62.5 |
| 4(c) | 4.0 | 250 | 31.0 |
| 6(b) | 8.0 | 250 | 31.0 |
| 9(b) | 31.0 | 250 | 31.0 |
| 10(b) | 62.5 | 250 | 31.0 |
| 11(b) | 8.0 | >500 | >500 |
| 12(d) | 16 | 250 | 31.0 |
| 14(d) | 31.0 | >500 | 125 |

We claim:

1. A pharmaceutical composition having enhanced antibacterial activity comprising a synergistically effective amount of a compound of formula (II):

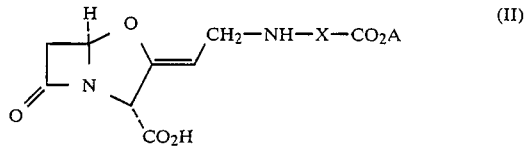

or a pharmaceutically acceptable salt or pharmaceutically acceptable ester thereof wherein A is a hydrogen atom or an esterifying radical; X is an alkylene group of 1–12 carbon atoms optionally substituted by a hydroxy, amino, formyl, $C_{1-6}$ alkanoyl, halo $(C_{1-6})$ alkanyl, acetyl or trifluoracetyl or $C_{1-6}$ alkoxy group, which substituents are not on the carbon atom adjacent the nitrogen atom; or a $C_{5-7}$ cycloalkyl group; or a phenylalkyl group wherein the carbon atom content of the alkyl part is 1–6 and the phenyl part is optionally substituted with a fluorine, bromine, chlorine, $C_{1-6}$ alkyl, or $C_{1-6}$ alkoxy; with the proviso that when X represents an optionally substituted phenylalkyl group and A represents $C_{1-3}$ alkyl, then the $-CO_2A$ group is attached to the alkyl part of the phenylalkyl group, together with an antibacterially effective amount of a penicillin and a pharmaceutically acceptable carrier.

2. A composition according to claim 1 wherein the penicillin is selected from benzylpenicillin, phenoxymethylpenicillin, carbenicillin, azidocillin, propicillin, ampicillin, amoxycillin, epicillin, ticarcillin, cyclacillin, pirbenicillin, azlocillin, mezlocillin, celbinicillin, or pharmaceutically acceptable in vivo hydrolysable esters thereof.

3. A composition according to claim 2 wherein the pharmaceutically acceptable penicillin esters are selected from acetoxymethyl, pivaloyloxymethyl, α-ethoxycarbonyloxyethyl or phthalidyl esters.

4. A composition according to claim 1 wherein the penicillins are aldehyde or ketone adducts containing a 6-α-aminoacetamide side chain.

5. A composition according to claim 4 wherein the aldehyde or ketone adduct is hetacillin or metampicillin.

6. A composition according to claim 2 wherein the pharmaceutically acceptable esters are the phenyl or indanyl α-esters of carbenicillin or ticarcillin.

7. A composition according to claim 1 wherein the penicillin is ampicillin or amoxycillin.

8. A composition according to claim 1 wherein the penicillin is in the form of a pharmaceutically acceptable salt or a hydrate.

9. A composition according to claim 1 which is in form suitable for oral or parenteral administration.

10. A composition according to claim 1 wherein the penicillin is present, with relation to the compound of formula (II), in the ratio of 10:1 to 1:10.

11. A pharmaceutical composition having enhanced antibacterial activity comprising a synergistically effective amount of 9-N-(2'-carboxyethyl) aminodeoxyclavulanic acid as synergist and an antibacterially effective amount of amoxycillin as the active antibiotic.

12. A method for the treatment of bacterial infections in humans or domestic mammals which comprises administering to such humans or domestic mammals an anti-infective amount of a composition according to claim 1.

* * * * *